(12) United States Patent
Rogers et al.

(10) Patent No.: US 9,248,928 B2
(45) Date of Patent: Feb. 2, 2016

(54) METHODS OF MANUFACTURING CONTACT LENSES FOR DELIVERY OF BENEFICIAL AGENTS

(71) Applicant: CooperVision International Holding Company, LP, St. Michael (BB)

(72) Inventors: Victoria Rogers, Pleasanton, CA (US); Andrew Luk, Pleasanton, CA (US); Arthur Back, Danville, CA (US); Charlie Chen, San Ramon, CA (US)

(73) Assignee: CooperVision International Holding Company, LP, St. Michael (BB)

( * ) Notice: Subject to any disclaimer, the term of this patent is extended or adjusted under 35 U.S.C. 154(b) by 64 days.

(21) Appl. No.: 14/109,978

(22) Filed: Dec. 18, 2013

(65) Prior Publication Data

US 2014/0179825 A1 Jun. 26, 2014

Related U.S. Application Data

(60) Provisional application No. 61/740,610, filed on Dec. 21, 2012.

(51) Int. Cl.
| | | |
|---|---|---|
| *B65B 23/00* | (2006.01) | |
| *C08L 33/10* | (2006.01) | |
| *A61F 9/00* | (2006.01) | |
| *A61K 47/48* | (2006.01) | |
| *G02C 7/04* | (2006.01) | |
| *A61K 9/00* | (2006.01) | |
| *G02B 1/04* | (2006.01) | |
| *B29D 11/00* | (2006.01) | |
| *B65B 25/00* | (2006.01) | |

(52) U.S. Cl.
CPC .............. *B65B 23/00* (2013.01); *A61K 9/0048* (2013.01); *A61K 47/48192* (2013.01); *B29D 11/00096* (2013.01); *G02B 1/043* (2013.01); *B65B 25/008* (2013.01)

(58) Field of Classification Search
None
See application file for complete search history.

(56) References Cited

U.S. PATENT DOCUMENTS

| | | | | |
|---|---|---|---|---|
| 5,760,100 A | * | 6/1998 | Nicolson et al. | 523/106 |
| 7,632,794 B1 | | 12/2009 | Xia et al. | |
| 2005/0056553 A1 | * | 3/2005 | Matsuzawa et al. | 206/5.1 |
| 2007/0149428 A1 | * | 6/2007 | Ammon et al. | 510/112 |
| 2008/0287395 A1 | * | 11/2008 | Ghosh et al. | 514/77 |
| 2008/0311070 A1 | * | 12/2008 | Burke et al. | 424/78.04 |
| 2010/0178317 A1 | * | 7/2010 | Burke et al. | 424/429 |

FOREIGN PATENT DOCUMENTS

WO 2007070653 A2 6/2007

OTHER PUBLICATIONS

International Search Report and Written Opinion issued in corresponding International Patent Application No. PCT/GB2013/053389 dated Apr. 4, 2014 (10 pages).

International Preliminary Report on Patentability issued in corresponding International Patent Application No. PCT/GB2013/053389 dated Dec. 11, 2014 (10 pages).

* cited by examiner

*Primary Examiner* — Peter A Salamon
(74) *Attorney, Agent, or Firm* — Kilyk & Bowersox, P.L.L.C.

(57) ABSTRACT

Contact lenses comprising an ionic component are packaged with a beneficial cationic agent in a temperature-sensitive packaging solution and/or a low ionic strength packaging solution.

20 Claims, No Drawings

METHODS OF MANUFACTURING CONTACT LENSES FOR DELIVERY OF BENEFICIAL AGENTS

This application claims the benefit under 35 U.S.C. §119 (e) of prior U.S. Provisional Patent Application No. 61/740,610, filed Dec. 21, 2012, which is incorporated in its entirety by reference herein.

BACKGROUND

The field of the disclosure is the manufacture of contact lenses for administering beneficial agents.

Methods of making contact lenses for administering ophthalmic drugs and other beneficial agents to the ocular tissue of a patient have been described. Some problems associated with prior art methods include inefficient use of the beneficial agent in that significantly more drug is required to make the lens than is actually delivered by the lens to the patient. Another problem is that the dimensions or physical properties of the lens may significantly change upon release of the agent from the drug. Yet another problem of prior art methods for manufacturing such lenses is that the methods are complex and not amenable to high volume manufacturing operations. We have discovered improved methods of manufacturing beneficial agent-releasing contact lenses that overcome the foregoing problems.

Contact lens packages including a sealed receptacle that contains a contact lens made of a silicone hydrogel copolymer in a sterile solution which comprises a stabilizing agent which can form an ionic complex or hydrogen bond with the hydrogel copolymer, have been described in U.S. Pat. Publ. No. 2007/0149428. A packaging system and method for the storage of an ionic hydrogel lens that uses an aqueous packing solution which includes a phosphorylcholine polymer, and which further can include a buffering agent, have been described in U.S. Pat. Publ. No. 2009/0100801. Other background publications include U.S. Pat. No. 7,811,601, U.S. Publ. No. 2008/0085922, U.S. Publ. No. 2010/0249356, U.S. Publ. No. 2008/0124376, U.S. Publ. No. 2008/0023345, U.S. Publ. No. 2009/0324691, U.S. Publ. No. 2007/0265247, Karlgard et al, Int J Pharm (2003) 257:141-51, and Soluri et al., Optom Vis Sci (2012) 89:1140-1149.

SUMMARY

An aspect of the invention is a method of manufacturing a contact lens, and the contact lenses made thereby, that can release a beneficial agent to ocular tissue of a patient who wears the lens. The method comprises polymerizing a monomer mixture comprising at least one carboxylic-acid containing monomer to form a lens-shaped polymerization product, placing the lens-shaped polymerization product in a package containing a packaging solution comprising a buffer and a beneficial cationic agent, and sealing and autoclaving the package to provide a sterile packaged contact lens. Advantageously, the beneficial cationic agent ionically binds to the carboxylic acid groups of the polymerization product and releases from the contact lens upon wear by a patient. The packaging solution has an osmolality of about 200 to about 400 mOsm/kg. In one example, the packaging solution further has an ionic strength of less than about 0.1, which facilitates uptake of the cationic agent from the packaging solution by the contact lens. In another example, the packaging solution is temperature-sensitive, meaning that its pH drops by at least one during autoclave at 120° C. for 30 minutes (e.g a drop from pH 7.5 to pH 6.5). Advantageously, certain beneficial cationic agents are autoclave-stable in a temperature-sensitive packaging solution, such as a TRIS-buffered packaging solution, whereas they are unstable (i.e. undergo appreciable degradation) in conventional packaging solutions, such as PBS. Advantageously, the beneficial cationic agent ionically binds to the carboxylic acid groups of the polymerization product and releases from the contact lens upon wear by a patient.

DETAILED DESCRIPTION

We have discovered improved methods of manufacturing contact lenses that can be used to administer beneficial agents to a patient. The method comprises packaging a hydrogel contact lens comprising carboxylic acid groups in a buffered solution comprising a cationic agent, and autoclaving the packaged lens. The buffered solution has an ionic strength of less than about 0.1, or is temperature-sensitive, or is both temperature-sensitive and has an ionic strength of less than about 0.1.

The hydrogel is prepared by polymerizing a monomer mixture comprising at least one carboxylic acid-containing monomer to form a polymerization product. As used herein, the term "monomer mixture" refers to a mixture of polymerizable monomers together with any additional ingredients, including non-polymerizable ingredients, which are subjected to polymerization conditions to form a polymerization product. The term "monomer" refers to any molecule capable of reacting in a polymerization reaction with other molecules that are the same or different, to form a polymer or copolymer. Thus, the term encompasses polymerizable pre-polymers and macromers, there being no size-constraint of the monomer unless indicated otherwise. Non-limiting examples of carboxylic acid-containing monomers that can be used include methacrylic acid, acrylic acid, itaconic acid, crotonic acid, cinnamic acid, vinylbenzoic acid, fumaric acid, maleic acid, monoesters of fumaric acid, and N-vinyloxycarbonyl-L-alanine. The term "carboxylic acid-containing monomer" also includes monomers that can undergo hydrolysis to provide a negative charge at about pH 7. For example, trimethysilyl methacrylate (TMSMA) may be included in a monomer mixture and polymerized. When the resulting polymerization product is hydrated, the trimethylsilyl group hydrolyses to generate methacrylic acid (i.e. the structure of a polymerized methacrylic acid monomer). The hydrogel may be a so-called "conventional hydrogel" meaning that the major component of the monomer mixture is a hydrophilic monomer such as 2-hydroxyethyl methacrylate (HEMA) or vinyl alcohol, together with the carboxylic acid-containing monomer and optionally other monomers, and contains no siloxane (i.e. a molecule comprising at least one Si—O group). Alternatively, the hydrogel may be a silicone hydrogel, meaning that the monomer mixture comprises at least one polymerizable siloxane monomer in addition to the carboxylic acid-containing monomer and optionally other monomers. An exemplary silicone hydrogel formulation is described in Example 1 below.

The amount of carboxylic acid-containing monomer included in the monomer mixture is selected to provide the desired uptake and release of the cationic agent. In one example, the carboxylic acid-containing monomer is included in the monomer mixture in an amount to provide the hydrogel with an ionic content of from about 0.1% 0.3%, 0.5%, 1.0%, or 1.5% up to about 2.0%, 2.2%, 2.5%, or 3.0%. As used herein a % ionic content is determined by the following equation: $(a \times b/c) \times 89 = \%$ ionic content, where a is the weight percentage of the carboxylic acid-containing monomer used in the monomer mixture, b is the number of negatively-charged groups on the carboxylic acid-containing monomer at pH 7, and c is the molecular weight of the carboxylic acid-containing monomer. As used herein, the weight percentage of a particular monomer in the monomer mixture is relative to the weight of all components of the monomer mixture that incorporate into the hydrogel. In other words, ingredients of the monomer mixture that do not incorporate into the final hydrogel product, such as diluents that are removed from the hydrogel during the manufacturing process, are not included in the weight percent determination. If more than one carboxylic acid-containing is used in a monomer mixture, the % ionic content of the hydrogel is the sum of the % ionic content provided by each carboxylic acid-containing. The above Formula I adjusts for differences in molecular weight and charge relative to methacrylic acid, which has a molecular weight of 89 and one ionic group. Thus, for example, the ionic content of a hydrogel prepared from a composition that comprises 2.0 wt. % of N-vinyloxy-carbonyl-L-alanine (MW=159, 1 ionic group) and no other anionic monomers is calculated as follows: $(2.0/159) \times (89) = 1.1\%$ ionic content. The ionic content of a hydrogel prepared from a composition that comprises 2.0 wt. % itaconic acid (MW=130, 2 ionic groups) and no other anionic monomers is calculated as follows: $(2.0 \times 2/130) \times 89 = 2.7\%$ ionic content. In specific examples, the hydrogel will not comprise any ionic monomers other than the carboxylic-acid containing monomer. Thus, for example, the monomer mixture will not comprise any monomers that comprise a phosphate group, or any group other than the carboxylic acid groups that provides the contact lens with a negative charge after packaging and sterilization.

As used herein, reference to "a", "an" or "the" monomer of a particular type (e.g. "the carboxylic-acid containing monomer") is meant to encompass "one or more" of said type of monomer unless context dictates otherwise. Thus, for example, a monomer mixture that comprises both N-vinyloxycarbonyl-L-alanine and methacrylic acid is understood to be a monomer mixture that comprises a carboxylic acid-containing monomer. In one example, methacrylic acid is the only ionic monomer in the monomer mixture, and the contact lens has an ionic content of 0.1% 0.3%, 0.5%, 1.0%, or 1.5% up to about 2.0%, 2.2%, 2.5%, or 3.0%. Throughout this disclosure a reference to "examples", "an example" or "a specific example" or similar phrase, is intended to introduce a feature or features of the contact lens, monomer mixture, packaging solution, method of manufacture, etc. (depending on context) that can be combined with any combination of previously-described or subsequently-described examples (i.e. features), unless a particular combination of features is mutually exclusive, or if context indicates otherwise.

Throughout this description, when a series of lower limit ranges and a series of upper limit ranges are provided, all combinations of the provided ranges are contemplated as if each combination were specifically listed. For example, in the listing of ionic content percentages in the previous paragraph, all 20 possible percent ionic content ranges are contemplated (i.e. 0.1-2.0%, 0.3-2.2% . . . 1.5%-2.5%, and 1.5%-3.0%). Further, throughout this disclosure, when a series of values is presented with a qualifier preceding the first value, the qualifier is intended to implicitly precede each subsequent value in the series unless context dictates otherwise. For example, for the values listed above, it is intended that the qualifier "from about" implicitly precedes the values 0.3, 0.5, 1.0, and 1.5, and the qualifier "up to about" implicitly precedes the values 2.2, 2.5, and 3.0. In a specific example, the ionic content of the hydrogel is in the range of 1.5% to 2.2%, or 1.6% to 2.0%.

The remaining components of the monomer mixture and method of polymerizing it can be conventional. Exemplary monomer mixture components and polymerization methods are described in U.S. Pat. No. 6,867,245, to Iwata et al., U.S. Pat. No. 8,129,442 to Ueyama et al., U.S. Pat. No. 4,889,664 to Kindt-Larsen et al., U.S. Pat. No. 3,630,200 to Higuchi, and U.S. Pat. No. 6,217,896 to Benjamin, and WO 2012/118680 to Liu et al, each incorporated herein by reference. The monomer mixture is filled into a contact lens mold, which is typically made from a thermoplastic polymer such as polypropylene. Typically, a first mold member defining the front surface of the contact lens, referred to as a "female mold member", is filled with an amount of the monomer mixture sufficient to form a single lens-shaped polymerization product. A second mold member defining the back (i.e. eye-contacting) surface of the contact lens, referred to as the "male mold member", is coupled to the female mold member to form a mold assembly having a lens-shaped cavity with the amount of monomer mixture in between the two mold members. The monomer mixture within the contact lens mold assembly is then polymerized using any suitable curing method. Typically, the monomer mixture is exposed to polymerizing amounts of heat or ultraviolet light (UV). In the case of UV-curing, also referred to as photopolymerization, the monomer mixture typically comprises a photoinitiator such as benzoin methyl ether, 1-hydroxycyclohexylphenyl ketone, Darocur or Irgacur (available from Ciba Specialty Chemicals). Photopolymerization methods for contact lenses are described in U.S. Pat. No. 5,760,100. In the case of heat-curing, also referred to as thermal curing, the monomer mixture typically comprises a thermal initiator. Exemplary thermal initiators include 2,2'-azobis(2,4-dimethylpentanenitrile) (V-52), 2,2'-Azobis(2-methylpropanenitrile) (V-64), and 1,1'-azo bis (cyanocyclohexane) (V-88). After cure, the mold is opened and the resulting lens-shaped polymerization product is either mechanically removed from the mold (i.e. dry-delensed) or is wet-delensed by immersing the mold in a liquid until the polymeric lens body hydrates and floats off of the mold. After delensing, the polymeric lens body may be washed to hydrate the lens and/or remove extractable components from the lens, or the lens may be placed directly into its final package containing a packaging solution, as detailed in the following paragraphs, without a post-delensing washing step. Thus, in one example, the lens is dry when placed into its final package. In another example, the lens may be partially or fully hydrated when placed in its final package. The package is then sealed and autoclaved. As used herein, the term "autoclave" is used to mean any heat-sterilization method suitable for sterilizing contact lenses.

The package may be a hermetically sealed blister-pack, in which a concave well containing a contact lens is covered by a metal or plastic sheet adapted for peeling in order to open the blister-pack. The package may be any other suitable inert packaging material providing a reasonable degree of protection to the lens, such as a glass vial or a package made from a plastic such as polyalkylene (e.g., polyethylene or polypropylene), PVC, polyamide, and the like. Generally, the final manufactured product includes at least a sealed package containing an unused contact lens immersed in an aqueous packaging solution as further exemplified herein.

The packaging solution comprises a beneficial cationic agent. As used herein, the term cationic agent refers to a covalently bonded molecule (i.e. as opposed to an ionically bonded salt) that has a net positive charge at the pH of the packaging solution. An agent is considered to have a net positive charge if it has more positively charged groups than negatively charged groups. For example, the ophthalmic drug olopatadine has a single positively charged tertiary amine group, and a single negatively charged carboxylic acid group, and thus is considered to have a net charge of zero. In one example, the cationic agent is a polymer. Exemplary cationic polymers include epsilon polylysine (ePLL), antimicrobial peptides comprising multiple arginine and/or lysine groups, polyquats, and the like. In a specific example, the cationic agent comprises a guanidinium group, which is a positively charged group comprising a central carbon atom covalently bonded to three nitrogen atoms, with a double bond between one of the nitrogen atoms and the central carbon. Exemplary beneficial agents for ophthalmic applications that comprise at least one guanidinium group include antihistamines such as epinastine and emedastine; glaucoma drugs such as apraclonidine and brimonidine; guanine derivative antiviral agents such as ganciclovir and valganciclovir; arginine-containing antimicrobial peptides such as the defensins and indolicidin; and biguanide-based antimicrobial agents such as chlorhexidine, alexidine, and polyhexamethylene biguanide (PHMB). Other beneficial cationic agents for ophthalmic application that can be included in the packaging solution include ketotifen, cationic steroids, and others.

We have found that by decreasing the ionic strength of the packaging solution from what is conventionally used for contact lenses, uptake of the cationic agent by the lens can be significantly increased. Examples 2 and 3 below demonstrate significantly increased uptake of a cationic polymer, epsilon poly-1-lysine (ePLL) by silicone hydrogel contact lenses (Example 2) and conventional hydrogel contact lenses (Example 3) when packaged in a low ionic strength packaging solution compared to conventional phosphate buffered saline (PBS). As used herein, PBS refers to a PBS having the formulation provided in Example 2 below, unless indicated otherwise. We also achieved significantly increased uptake of the non-polymeric cationic drug, epinastine, by decreasing the ionic strength of the packaging solution. For example when the silicone hydrogel contact lens described in Example 1 below was autoclaved in 3 ml TRIS buffered saline (ionic strength ~0.16) comprising 50 ppm epinastine, the lens took up about 56 μg of epinastine, which was about 37% of the available epinastine. When the salt (NaCl) in the TRIS buffer was replaced with sorbitol at a concentration of 2%, to provide a packaging solution having an ionic strength of about 0.02, the lenses took up about 88 μg epinastine, which was about 59% of the available epinastine. Thus, in various examples, the packaging solution has an ionic strength of less than about 0.10, 0.08, 0.06, or 0.04 as calculated by the equation:

$$I = \frac{1}{2}\sum_{i=1}^{n} c_i z_i^2$$

where $c_i$ is the molar concentration of ion i (mol·dm$^{-3}$), $z_i$ is the charge number of that ion and the sum is taken over all ions in the packaging solution.

To reduce ionic strength while maintaining proper osmolality in the range of about 200 mOsm/kg to about 400 mOsm/kg, sodium chloride, which is commonly used as a tonicity agent in contact lens packaging solutions, can be replaced with a non-electrolyte tonicity agent, such as sorbitol, as indicated above. Other non-electrolyte tonicity agents that can be used in the packaging solution include mannitol, sucrose, glycerol, propylene glycol, xylitol, inositol, polyethylene glycols, polypropylene glycols, and mixtures thereof. In some examples, the osmolality of the packaging solution is at least about 250 or 270 mOsm/kg up to about 310, or 350 mOsm/kg. In some examples, the packaging solution consists of, or consists essentially of, an aqueous solution of a buffer, a tonicity agent, and the cationic agent. In other examples, the packaging solution contains additional agents such as an antimicrobial agent, a comfort agent, a hydrophilic polymer, or a surfactant or other additive that prevents the lens from sticking to the package. The packaging solution typically has a pH in the range of about 6.8 or 7.0 up to about 7.8 or 8.0. In various examples, the packaging solution has an ionic strength of less than about 0.10 and the lens takes up at least 20%, 50%, or 100% more of the cationic agent than an identical lens packaged in PBS comprising the same concentration of the cationic agent. As used herein, the amount of cationic agent taken up by a lens is calculated by the following equation: $(C_n-C_l) \times V$, wherein $C_n$ is the concentration of cationic agent in the packaging solution autoclaved without a lens minus, $C_l$ is the concentration of cationic agent in the packaging solution autoclaved with a lens, and V is the volume of packaging solution, wherein the cationic agent concentration is measured by an analytical method suitable for quantification of the particular cationic agent (e.g. HPLC).

We have observed that some cationic agents are not autoclave-stable in PBS, which is a common contact lens packaging solution. As used herein, a cationic agent is considered to be autoclave-stable in a given package and packaging solution if there is less than 2% degradation of the cationic agent after it is autoclaved two times in its intended package and packaging solution without a lens present, wherein the autoclave conditions used are 120° C. for 30 minutes at about 17 psi. A reference to 2× or 3× autoclave of a package is intended to include a step of allowing the package to cool to room temperature before and after the $2^{nd}$, and if applicable, $3^{rd}$ autoclave treatments. The amount of degradation is determined using an HPLC method appropriate for the cationic agent being tested. Alternatively or additionally, a cationic agent is considered autoclave-stable in a given packaging solution if the percentage of cationic agent that can be extracted from the lens after 2× autoclave is more than 95% of the percentage of cationic agent that can be extracted from a non-autoclaved lens packaged in the same packaging solution and kept at room temperature for 24 hours, where the extraction method used is substantially as described in Example 4, or an equivalent method. The percentage of cationic agent extracted from the autoclaved (test) and non-autoclaved (control) lenses is determined relative to the amount of cationic agent taken up by the test and control lenses, respectfully. Thus, for example, a control lens may take up 100 μg of a cationic agent from a packaging solution after 24 hours at room temperature and 97 μg (i.e. 97%) of the cationic agent can be extracted from the lens. If the corresponding test (2× autoclaved) lens takes up 120 μg of the cationic agent from the packaging solution, but only 108 μg (i.e. 90%) of the cationic agent is extracted using the same extraction method as for the control lens, then there is considered to be a 7% difference between the amount cationic agent extracted from control and test lenses. Because this difference is ≥5%, with the percentage of cationic agent extracted from the test lens being less than that extracted from the control lens, the cationic agent is considered to be not autoclave-stable in the packaging solution even though the total amount of cationic agent extracted from the test lens is more than what is extracted from the control lens.

In Example 4 below, we show that epinastine is not autoclave-stable in PBS, but is autoclave-stable in a TRIS buffer. By comparison, we found that other ionic anti-allergy ophthalmic drugs, specifically olopatadine HCl and ketotifen fumarate, were autoclave-stable in PBS. We also show in Example 5 below that ePLL is not autoclave-stable in PBS, but is autoclave-stable in a TRIS buffer. Both ePLL and epinastine have primary amine groups, whereas olopatadine and ketotifen have none. Our hypothesis is that during autoclave at pH 7 certain amine-containing compounds undergo some degradation and/or reaction with the lens material. TRIS buffer drops in pH with increased temperature, down to a pH of about 4.3 during autoclave. This lower pH may prevent the reaction or degradation that happens to amine-containing compounds during autoclave in PBS. Thus, in one example, the packaging solution used in the method of manufacturing the contact lenses described herein is temperature-sensitive. By temperature-sensitive, it is meant that the pH of the packaging solution drops by at least one (e.g a drop from pH 7.5 to pH 6.5) during autoclave at 120° C. for 30 minutes. In specific examples, the pH of the temperature-sensitive packaging solution drops during autoclave by at least 1.5, 2.0, or 2.5. Exemplary temperature-sensitive buffers include {[tris(hydroxymethyl)methyl]amino}propanesulfonic acid (TAPS), N,N-bis(21-hydroxyethyl)glycine (Bicine), tris(hycroxymethyl)methylamine (TRIS), N-tris(hydroxymethyl) methylglycine (Tricine), {[tris(hydroxymethyl)methyl] amino}ethanesulfonic acid (TES), 3-(N-morpholino) propanesulfonic acid (MOPS), and the like. Thus, in various examples of the methods described herein, the packaging solution is temperature-sensitive and the cationic agent is autoclave-stable in the temperature-sensitive packaging solution and is not autoclave-stable in PBS. In one such example, the packaging solution comprises a TRIS buffer. In a further example, the cationic agent comprises a primary amine. In yet a further example, the cationic agent is epinastine or εPLL and the packaging solution comprises a TRIS buffer.

The contact lenses described herein have cationic agent ionically bound to the carboxylic acid groups which release from the contact lens in an in vitro release assay. As used herein, an in vitro release assay is substantially as described in Example 2 below, where a lens is immersed in 1 ml of ISO 10344 standard saline solution (release medium) in a suitable container in which the lens can remain fully immersed in the saline during shaking (e.g. a well of a 12-well plate, or a glass or plastic lens vial). The container is shaken at 100 rpm at 37±2° C., and the release medium is sampled at 2, 4, 8, 24 and 48 hours and tested by HPLC for the presence of the cationic agent. The release medium is replaced with fresh release medium at each time point tested until there is no significant increase in concentration of the cationic agent in the release medium from one time point to the next. A lens is considered to release the cationic agent if a significant amount of the agent is detectable in the release medium sampled at the 2 hour time point using this method. In various examples, the lens releases a total of at least 5, 10, 25, 50, 75% of the cationic agent that was taken up by the lens. In certain examples the lens releases 95% or even 100% of the cationic agent taken up by the lens. In some examples, the lens may sustain release of the cationic agent. As used herein, a lens is considered to sustain release of a cationic agent if a significant amount of the agent is detectable in the release medium sampled at the 4 hour time point in the in vitro release assay. In this case, the lens is said to sustain release of the cationic agent for at least two hours. In some cases, the lens may sustain release of the cationic agent for at least 4, 8, or 24 hours. For example, if a significant amount of the cationic agent is detectable in the release medium sampled at the 24 hour time point, the lens is said to sustain release of the cationic agent for at least 8 hours.

We have found that carboxylic-acid containing hydrogel contact lenses as described herein have good dimensional stability and can uptake and release cationic agents without significant alteration to the dimensions of the lens (e.g. lens diameter and base curve) or other physical properties of the lens.

The cationic agent-eluting contact lenses described herein, after having been worn by a patient, may be stored in a solution comprising an additional dose of the cationic agent. The storage solution has an osmolality of about 200 to about 400 mOsm/kg and has an ionic strength of less than about 0.1, allowing the additional dose of the cationic agent to ionically bind to the carboxylic acid groups of the contact lens, thereby replenishing the cationic agent released during the previous wear by the patient. The storage solution may comprise additional components that assist in sterilizing or cleaning the lens, such as components typically used in multipurpose contact lens care solutions.

The following Examples illustrate certain aspects and advantages of the present invention, which should be understood not to be limited thereby.

Example 1

Preparation of Anionic Silicone Hydrogel Contact Lenses

A monomer mixture was prepared by weighing and mixing together the chemicals listed in Table 1 below in the relative parts (by weight) indicated and filtered using a 0.2-5.0 micron filter. The mono-functional siloxane listed in the Table 1 has structure II shown below. Methods of making this siloxane monomer are described in U.S. Pat. No. 8,168,735 to Ichinohe.

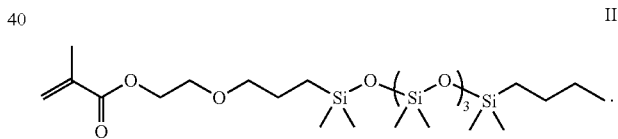

II

The bi-functional siloxane macromer listed in Table 1 has structure III shown below, wherein n is about 90, m is about 5 and p is about 7.0. Methods of making this macromer are described in U.S. Pat. No. 8,129,442 to Ueyama et al.

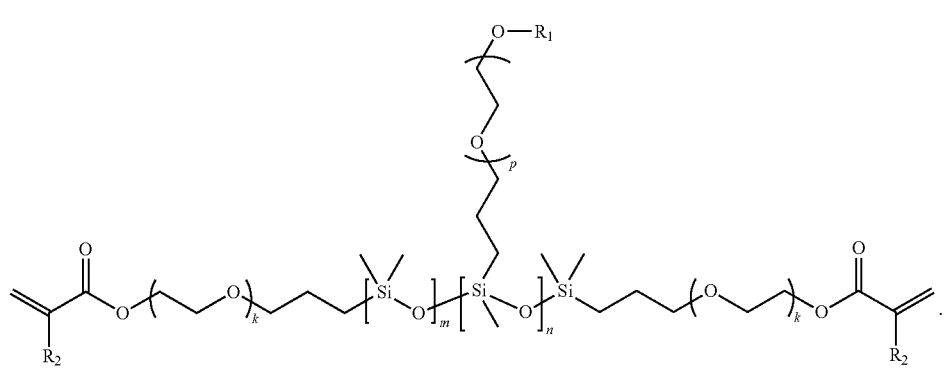

III

TABLE 1

| Chemical | Parts by wt. |
| --- | --- |
| methacrylic acid | 1.8 |
| mono-functional siloxane monomer | 29 |
| bi-functional siloxane macromer | 8 |
| N-vinyl-N-methylacetamide | 45 |
| methyl methacrylate | 8 |
| diethylene glycol vinyl ether | 5 |
| ethylene glycol methyl ether methacrylate | 6 |
| ethylene glycol dimethacrylate | 0.6 |
| triethyleneglycol divinyl ether | 0.1 |
| Norbloc (CAS no. 96478-09-0) | 1.7 |
| Diphenyl (P-vinylphenyl) phosphine (CAS no. 40538-11-2) | 0.5 |
| Reactive Blue 247 (CAS Reg. No. 109561-07-1) | 0.01 |
| Vazo-64 (CAS reg. No. 78-67-1) | 0.5 |
| 2-Allyloxy ethanol | 0.8 |

The resulting polymerizable monomer mixture was cast molded in polypropylene contact lens mold assemblies and thermally cured in a nitrogen oven using conventional methods. Each cured lens was removed from its mold and hydrated and washed using multiple exchanges of deoinized water to remove unreacted and partially reacted components from the hydrogel.

Example 2

Affect of Ionic Strength of Packaging Solution on ePLL Uptake by Ionic Silicone Hydrogel Contact Lenses Lenses made according to Example 1 were transferred to 6 ml glass vials containing 1.2 ml 500 ppm ePLL in phosphate buffered saline (PBS) having an ionic strength of about 0.20, or a TRIS buffer with 2% sorbitol having an ionic strength of about 0.02. As used herein, references to PBS mean a solution having a pH of about 7.5 comprising 0.78 wt. % NaCl, 0.05 wt. % sodium phosphate monobasic, 0.36 wt. % sodium phosphate dibasic, and 98.81% deionized water, unless indicated otherwise. The TRIS buffer used in this experiment had the following formulation: 0.02% tris(hydroxymethyl) amino methane, 0.27% trizma hydrochloride, 1.96% sorbitol, and 97.75% deionized water. The vials were sealed and autoclaved at 120° C. for 30 minutes. Additionally, vials containing 1.2 ml 500 ppm ePLL in PBS with no lens (control vial) were also autoclaved. The amounts of ePLL present in the post-autoclave solution of the test lens vial and in the control vial were determined by cationic size exclusion chromatography using a sample injection volume of 20 µl, an Eprogen CATSEC300 5µ 250×4.6 MM, at room temperature, and a flow rate of 1.0 ml/min using 0.2M NaCl/0.1% TFA in $H_2O$ isocratically. The amount of ePLL taken up by the lenses was calculated by subtracting the amount of ePLL present in the post-autoclave solution of the test lens vial from the amount of ePLL present in the control vial. The lenses packaged in PBS took up an average of 191 µg ePLL from the packaging solution, which was about 32% of the total ePLL available in the packaging solution. The lenses packaged in the TRIS/sorbitol buffer took up an average of 408 µg ePLL, which was about 68% of the total ePLL available in the packaging solution.

Example 3

Effect of Ionic Strength of Packaging Solution on ePLL Uptake by HEMA-Based Hydrogel Contact Lenses An ocufilcon D monomer mixture (HEMA with about 1.8% methacrylic acid, a cross-linker, and a polymerization initiator) was cured in polypropylene molds. The lenses were removed from their molds and, without prior hydration, placed into glass vials containing 1.2 ml of 500 ppm ePLL in either PBS, TRIS buffered saline (0.02% tris(hydroxymethyl) amino methane, 0.27% trizma hydrochloride, 0.82% NaCl, 98.88% deionized water) or TRIS buffer (pH 7) with 2% sorbitol (0.02% tris(hydroxymethyl) amino methane, 0.27% trizma hydrochloride, 3.0% sorbitol, 96.75% deionized water). The lenses were autoclaved and evaluated for ePLL uptake as described in Example 2 above. The lenses packaged in the PBS, which has an ionic strength of about 0.20, took up an average of 115 µg ePLL, which was approximately 20% of the total ePLL available in the packaging solution. The lenses packaged in the TRIS buffered saline, which has an ionic strength of about 0.16, took up an average of 263 µg ePLL, which was approximately 44% of the total ePLL available in the packaging solution. The lenses packaged in the TRIS-sorbitol buffer, which has an ionic strength of about 0.02, took up an average of about 611 µg ePLL, which was essentially all of ePLL in the packaging solution.

In Vitro Release Assay:

The lenses were tested for their ability to release the ePLL into a saline solution. Excess solution was removed from each lens by gently blotting with an absorbent tissue. Each lens was immersed in 1 ml of ISO 10344 standard saline solution (0.83% sodium chloride, 0.0467% sodium phosphate monobasic, and 0.4486% sodium phosphate dibasic) in glass vials. The vials were shaken at 100 rpm at 37±2° C. At 2, 4, 6, 8, 24, and 48 hours, the solution was removed from each vial and replaced with 1 ml of fresh ISO 10344 standard saline solution. HPLC was used to determine the amount of ePLL released from each lens. Table 2 shows the average cumulative amount (in µg) of ePLL released from the lens at each time point as well as the cumulative percentage of ePLL released relative to total amount of ePLL taken up by the lens.

TABLE 2

| | TRIS-NaCl | | TRIS-Sorbitol | |
| --- | --- | --- | --- | --- |
| time (hr) | µg release | % released | µg release | % released |
| 2 | 75 | 28 | 284 | 47 |
| 4 | 105 | 40 | 341 | 56 |
| 8 | 132 | 50 | 380 | 62 |
| 24 | 163 | 62 | 416 | 68 |
| 48 | 178 | 68 | 431 | 71 |

Example 4

Autoclave Stability of Epinastine-Eluting Contact Lenses

Silicone hydrogel lenses prepared according to Example 1 and ocufilcon D that had been washed and hydrated to remove unreacted monomers were packaged in 6 ml glass vials containing 1.2 ml PBS comprising 200 µg/ml epinastine HCl. The packaged lenses were either autoclaved once or twice for 20 minutes at 120° C. and then kept at room temperature overnight, or kept at room temperature overnight without autoclaving. 1.2 ml PBS comprising 200 µg/ml epinastine HCL was autoclaved once or twice in a glass vial without a lens (autoclave control solution).

Uptake Assay:

After autoclave or equilibrium, the amount of epinastine taken up by the autoclaved lenses was calculated as 1.2× the difference between the epinastine concentration of the 1× or 2× autoclave control solution and the epinastine concentration of the packaging solution of the 1× or 2× autoclaved lens, respectively. The amount of epinastine taken up by the non-autoclaved lens was calculated as 1.2× the difference between 200 μg/ml and the concentration of epinastine in the packaging solution of the non-autoclaved lens. The amount of epinastine in each packaging solution was determined by HPLC.

Extraction Assay:

Each lens was blotted dry with lint-free paper, and placed in a vial containing 10 ml of an extraction medium consisting of 60 parts of 0.3% triethylamine in deionized (pH adjusted to 4.0 using phosphoric acid) and 40 parts methanol. The vials were sonicated for 30 minutes at room temperature. The lens were removed from the extraction solution and transferred to individual vials containing 5 ml of fresh extraction medium and sonicated again for 30 minutes. For each lens, the extraction media was combined to obtain 15 ml extraction medium for each lens and the amount of epinastine extracted from each lens was measured by HPLC. The results are shown in Table 3. For certain cationic agents, the extraction assay will include a third 30-minute sonication step in 5 ml fresh extraction medium if the additional extraction step results in significantly more cationic agent being extracted.

TABLE 3

| Lens Material | Autoclaved | | | | Non-Autoclaved | | | |
|---|---|---|---|---|---|---|---|---|
| | Uptake Amt. (μg) | Extr. Amt. (μg) | Δ (μg) | % Δ | Uptake Amt. (μg) | Extr. Amt. (μg) | Δ (μg) | % Δ |
| Ocufilcon D | 258.9 | 240.4 | 18.5 | 7% | 249.1 | 243.5 | 5.6 | 2% |
| Silicone hydrogel | 204.6 | 184.5 | 20.1 | 10% | 183.0 | 181.7 | 1.3 | 1% |
| Silicone hydrogel (2× autoclave) | 199.6 | 163.4 | 36.3 | 18% | | | | |

The results showed that the autoclaved ocufilcon D and silicone hydrogel lenses released about 93% and 90%, respectively, of the amount of epinastine taken up by the lens. In contrast, the corresponding non-autoclaved control lenses released 98% and 99%, respectively, of the amount of epinastine taken up by the lens. When the silicone hydrogel lenses were autoclaved a second time, only about 82% of the amount of epinastine taken up by the lens released, suggesting that a reaction between the epinastine and lens occurs during autoclave in PBS.

The study was repeated using silicone hydrogel contact lenses prepared according to Example 1 and packaged in TRIS buffer (described above) comprising 150 μg/ml epinastine. The lenses were autoclaved 0-3 times each. The results shown in Table 4 indicate that epinastine is autoclave-stable in TRIS buffer.

TABLE 4

| Autoclave # | Uptake mt. (μg) | Extracted Amt. (μg) | Δ (μg) | % Δ |
|---|---|---|---|---|
| 0 | 148.4 | 148.1 | 0.3 | 0.2% |
| 1× | 150.5 | 148.6 | 1.9 | 1.3% |
| 2× | 147.3 | 145.4 | 1.9 | 1.3% |
| 3× | 88.5 | 85.9 | 2.6 | 3.0% |

Example 5

Autoclave Stability of ϵPLL-Eluting Contact Lenses

Vials containing 500 ppm ϵPLL in 1.2 ml PBS or TRIS buffered saline (0.023% tris(hydroxymethyl)methylamine, 0.544% trizma hydrochloride, 0.819% NaCl; TBS) were autoclaved 0, 2 or 4 times. The samples were tested by HPLC at a sufficient resolution to achieve a discernable peak for each molecular weight fraction of the ϵPLL. The results are shown in Table 5.

TABLE 5

| Buffer | # Autoclaves | Total # peaks | Total peak area | % Area (relative to non-autoclaved) |
|---|---|---|---|---|
| PBS | 0 | 23 | 16005557 | — |
| PBS | 2 | 28 | 14566887 | 91% |
| PBS | 4 | 28 | 14468122 | 90% |
| TBS | 9 | 23 | 14800289 | — |
| TBS | 2 | 27 | 14636372 | 99% |
| TBS | 4 | 27 | 14476291 | 98% |

Although the disclosure herein refers to certain illustrated examples, it is to be understood that these examples are presented by way of example and not by way of limitation. The intent of the foregoing detailed description, although discussing exemplary examples, is to be construed to cover all modifications, alternatives, and equivalents of the examples as may fall within the spirit and scope of the invention as defined by the additional disclosure.

A number of publications and patents have been cited hereinabove. Each of the cited publications and patents are hereby incorporated by reference in their entireties.

The invention further provides:

1. A method of manufacturing a contact lens, said method comprising: a) polymerizing a monomer mixture comprising at least one carboxylic-acid containing monomer to form a lens-shaped polymerization product comprising carboxylic acid groups; b) placing the lens-shaped polymerization product in a package containing a packaging solution comprising a buffer and a beneficial cationic agent, wherein said packaging solution has an osmolality of about 200 to about 400 mOsm/kg, and wherein said packaging solution i) has an ionic strength of less than about 0.1, and/or ii) is temperature-sensitive, meaning that its pH drops by at least one during autoclave at 120° C. for 30 minutes (e.g a drop from pH 7.5 to pH 6.5); and c) sealing and autoclaving the package to provide a sterile packaged contact lens. Advantageously, the beneficial cationic agent ionically binds to the carboxylic acid groups of the polymerization product and releases from the contact lens upon wear by a patient.

2. The method of 1, wherein the carboxylic-acid containing monomer is methacrylic acid.

3. The method of 1, wherein the contact lens comprises from about 0.5 to about 2.5% methacrylic acid.

4. The method of 2 or 3, wherein the methacrylic acid is the only ionic monomer in the monomer mixture.

5. The method of any one of 1 to 4, wherein the monomer mixture comprises a silicone monomer.

6. The method of any one of 1 to 5, wherein the monomer mixture comprises 2-hydroxyethyl methacrylate.

7. The method of any one of 1 to 6, wherein at least 50% more of the cationic agent is taken up by the lens compared to an identical contact lens packaged in PBS.

8. The method of any one of 1 to 7, wherein the ionic strength of the packaging solution is less than 0.1.

9. The method of any one of 1 to 8, wherein the ionic strength of the packaging solution is less than 0.06.

10. The method of any one of 1 to 9, wherein in the packaging solution comprises a non-electrolyte tonicity adjusting agent.

11. The method of 10, wherein the tonicity adjusting agent is sorbitol.

12. The method of any one of 1 to 11, wherein the packaging solution has an osmolality of about 270 to about 310 mOsm/kg.

13. The method of any one of 1 to 12, wherein the cationic agent is a polymer.

14. The method of any one of 1 to 12, wherein the cationic agent is an ophthalmic drug.

15. The method of any one of 1 to 14, wherein the packaging solution is temperature-sensitive and the cationic agent is autoclave-stable in the packaging solution and is not autoclave-stable in PBS.

16. The method of any one of 1 to 15, wherein the packaging solution comprises a buffering agent selected from {[tris (hydroxymethyl)methyl]amino}propanesulfonic acid (TAPS), N,N-bis(21-hydroxyethyl)glycine (Bicine), tris(hycroxymethyl)methylamine (TRIS), N-tris(hydroxymethyl) methylglycine (Tricine), [tris(hydroxymethyl)methyl] amino}ethanesulfonic acid (TES), 3-(N-morpholino) propanesulfonic acid (MOPS), and any combination thereof.

17. The method of any one of 1 to 16, wherein the packaging solution comprises a TRIS buffer.

18. The method of any one of 1 to 17, wherein the cationic agent comprises a primary amine.

19. The method of any one of 1 to 17, wherein the cationic agent is epinastine and/or εPLL.

20. The method of any one of 1 to 19, further comprising storing the contact lens after it has been worn by a patient in a multi-purpose contact lens care solution (MPS) that comprises an additional amount of the cationic agent, wherein the storage solution has an osmolality of about 200 to about 400 mOsm/kg and has an ionic strength of less than about 0.1, wherein the additional cationic agent incorporates into the contact lens during the storage.

21. A contact lens made by the method of any one of 1 to 19.

We claim:

1. A method of manufacturing a contact lens, said method comprising:
   a) polymerizing a monomer mixture comprising at least one carboxylic-acid containing monomer to form a lens-shaped polymerization product comprising carboxylic acid groups;
   b) placing the lens-shaped polymerization product in a package containing a packaging solution comprising a buffer and a beneficial cationic agent, wherein said packaging solution has an osmolality of about 200 to about 400 mOsm/kg, and wherein said packaging solution i) has an ionic strength of less than about 0.1, or ii) is temperature-sensitive, or iii) has an ionic strength of less than about 0.1 and is temperature-sensitive; and
   c) sealing and autoclaving the package to provide a sterile packaged contact lens, wherein the beneficial cationic agent ionically binds to the carboxylic acid groups and releases from the contact lens in an in vitro release assay; wherein at least 50% more of the cationic agent is taken up by the lens compared to an identical contact lens packaged in PBS.

2. The method of claim 1, wherein the carboxylic-acid containing monomer is methacrylic acid.

3. The method of claim 1, wherein the contact lens comprises from about 0.5 to about 2.5% methacrylic acid.

4. The method of claim 3, wherein the methacrylic acid is the only ionic monomer in the monomer mixture.

5. The method of claim 1, wherein the monomer mixture comprises a silicone monomer.

6. The method of claim 1, wherein the monomer mixture comprises 2-hydroxyethyl methacrylate.

7. The method of claim 1, wherein the ionic strength of the packaging solution is less than 0.1.

8. The method of claim 1, wherein the ionic strength of the packaging solution is less than 0.06.

9. The method of claim 1, wherein in the packaging solution comprises a non-electrolyte tonicity adjusting agent.

10. The method of claim 9, wherein the tonicity adjusting agent is sorbitol.

11. The method of claim 1, wherein the packaging solution has an osmolality of about 270 to about 310 mOsm/kg.

12. The method of claim 1, wherein the cationic agent is a polymer.

13. The method of claim 1, wherein the cationic agent is an ophthalmic drug.

14. The method of claim 1, wherein the packaging solution comprises a temperature-sensitive buffer and the cationic agent is autoclave-stable in the packaging solution and is not autoclave-stable in PBS.

15. The method of claim 14, wherein the temperature-sensitive buffer comprises a buffering agent selected from {[tris(hydroxymethyl)methyl]amino}propanesulfonic acid (TAPS), N,N-bis(21-hydroxyethyl)glycine (Bicine), tris(hycroxymethyl)methylamine (TRIS), N-tris(hydroxymethyl) methylglycine (Tricine), [tris(hydroxymethyl)methyl] amino}ethanesulfonic acid (TES), 3-(N-morpholino) propanesulfonic acid (MOPS), and any combination thereof.

16. The method of claim 14, wherein the temperature-sensitive buffer comprises a TRIS buffer.

17. The method of claim 14, wherein the cationic agent comprises a primary amine.

18. The method of claim 14, wherein the cationic agent is epinastine and/or εPLL.

19. The method of claim 1, further comprising storing the contact lens after it has been worn by a patient in a multi-purpose contact lens care solution (MPS) that comprises an additional amount of the cationic agent, wherein the storage solution has an osmolality of about 200 to about 400 mOsm/kg and has an ionic strength of less than about 0.1, wherein the additional cationic agent incorporates into the contact lens during the storage.

20. A contact lens made by the method of claim 1.

* * * * *

UNITED STATES PATENT AND TRADEMARK OFFICE
CERTIFICATE OF CORRECTION

| | | |
|---|---|---|
| PATENT NO. | : 9,248,928 B2 | Page 1 of 1 |
| APPLICATION NO. | : 14/109978 | |
| DATED | : February 2, 2016 | |
| INVENTOR(S) | : Rogers et al. | |

It is certified that error appears in the above-identified patent and that said Letters Patent is hereby corrected as shown below:

IN THE CLAIMS:

Claim 15, lines 4-5, "tris(hycroxymethyl)methylamine" should read
--tris(hydroxymethyl)methylamine--.

Signed and Sealed this
Twelfth Day of April, 2016

Michelle K. Lee
*Director of the United States Patent and Trademark Office*